United States Patent [19]
Whelan et al.

[11] Patent Number: 5,976,181
[45] Date of Patent: Nov. 2, 1999

[54] BALLOON MOUNTED STENT AND METHOD THEREFOR

[75] Inventors: Sean Whelan, Galway; Neil Purcell, Gallway; Thomas Fitzmaurice, Galway, all of Ireland

[73] Assignee: AVE Connaught, Santa Rosa, Calif.

[21] Appl. No.: 08/934,703

[22] Filed: Sep. 22, 1997

[51] Int. Cl.$^6$ .............................. A61F 2/06; A61M 29/00
[52] U.S. Cl. ................. 623/1; 606/195; 606/194
[58] Field of Search .................. 623/1, 12, 901; 606/108, 192, 194–195, 198

[56] References Cited

U.S. PATENT DOCUMENTS

| | | | |
|---|---|---|---|
| 4,762,128 | 8/1988 | Rosenbluth | 606/198 |
| 5,108,416 | 4/1992 | Ryan et al. . | |
| 5,158,548 | 10/1992 | Lau et al. . | |
| 5,242,399 | 9/1993 | Lau et al. . | |
| 5,250,070 | 10/1993 | Parodi | 606/194 |
| 5,282,823 | 2/1994 | Schwartz et al. | 606/198 |
| 5,484,449 | 1/1996 | Amundson et al. | 606/108 |
| 5,490,839 | 2/1996 | Wang et al. | 606/192 |
| 5,571,135 | 11/1996 | Fraser et al. . | |
| 5,746,745 | 5/1998 | Abele et al. | 623/1 |
| 5,755,722 | 5/1998 | Barry et al. | 606/108 |
| 5,792,172 | 8/1998 | Fischell et al. . | |
| 5,836,965 | 11/1998 | Jendersee et al. . | |

FOREIGN PATENT DOCUMENTS

| | | |
|---|---|---|
| 0 770 366 A1 | 5/1997 | European Pat. Off. . |
| 0 778 010 A2 | 6/1997 | European Pat. Off. . |
| 0 834 293 A1 | 4/1998 | European Pat. Off. . |
| 2 753 907 | 4/1998 | France . |

*Primary Examiner*—Bruce E. Snow
*Attorney, Agent, or Firm*—Sterne, Kessler, Goldstein & Fox P.L.L.C.

[57] ABSTRACT

The present invention concerns a mechanism for securely mounting an expandable stent onto a balloon catheter for intraluminal delivery within a patient. The stent is secured to the balloon of the delivery catheter by forming the surface of the balloon to project into the interstices of the stent. To mount the stent it first is slid over an evacuated and wrapped balloon while in its compact delivery diameter. A rigid tube then is placed over the stent and balloon assembly and the balloon is pressurized while a solvent is applied to the balloon. The rigid tube prevents the stent from expanding but allows the balloon to deform so that its surface projects slightly through either or both of the interstices and ends of the stent. The solvent causes the balloon material to take a permanent set into the stent such that once pressure is removed, the stent is interlocked with the surface of the balloon. The engagement of the stent with the balloon prevents unintended axial sliding of the stent with respect to the balloon during delivery through the vessel of the patient.

5 Claims, 3 Drawing Sheets

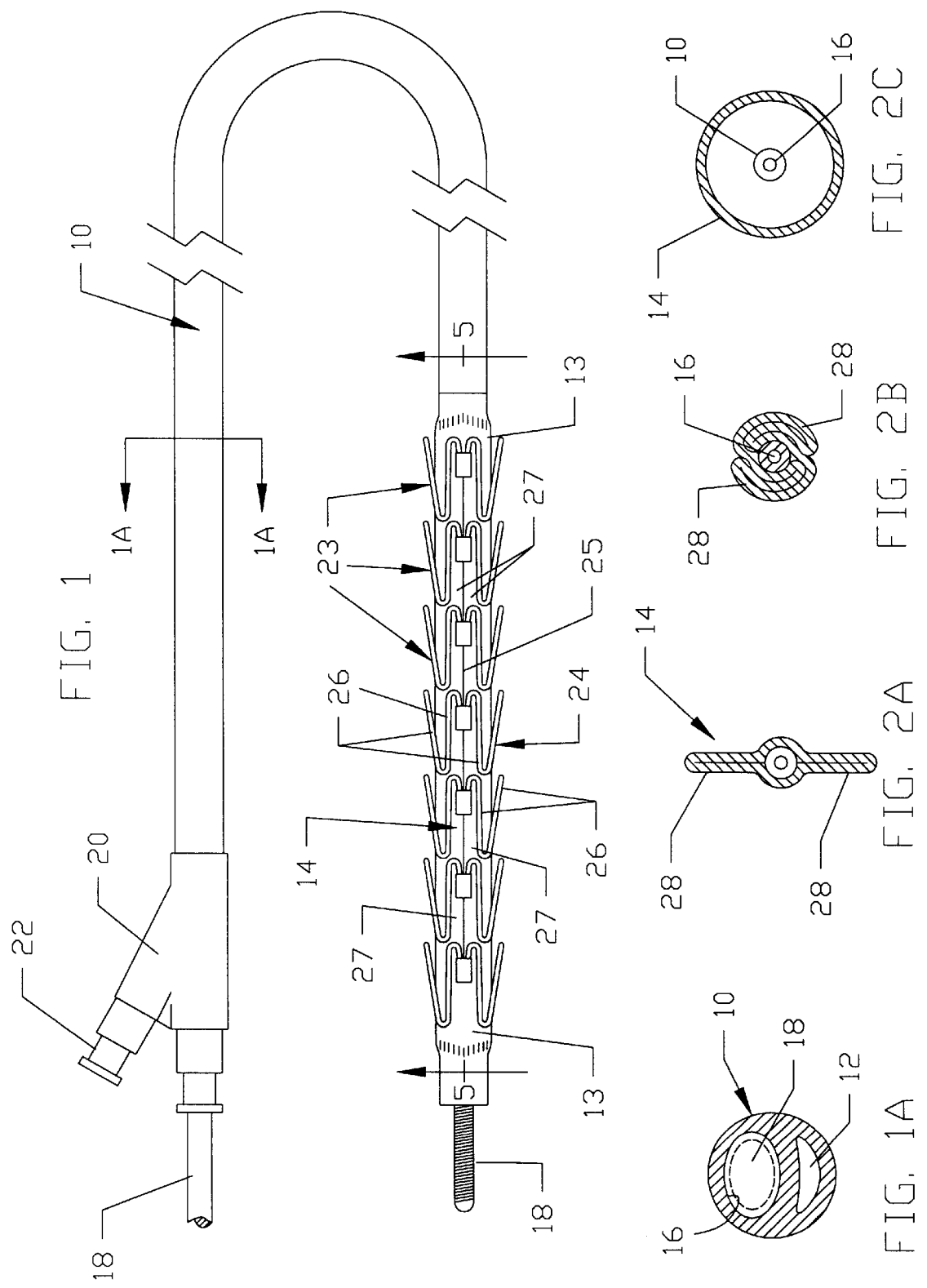

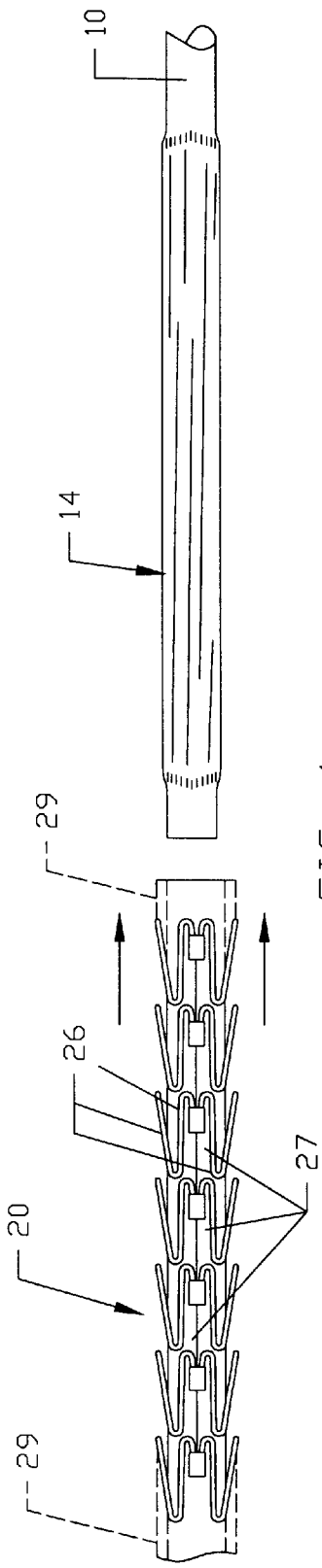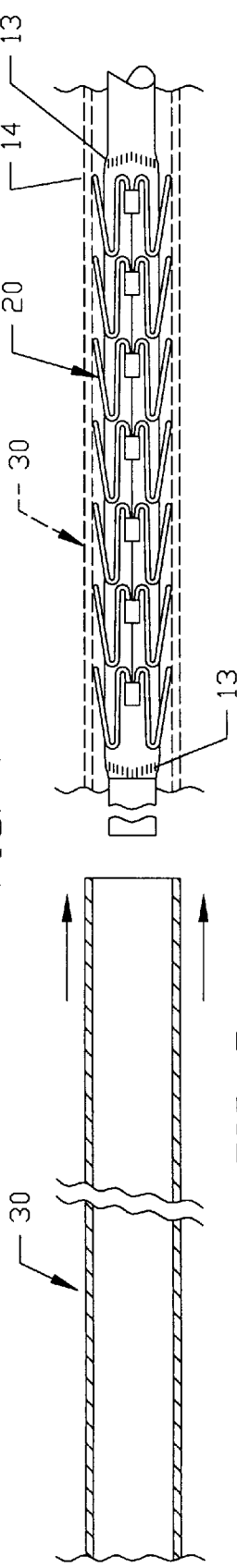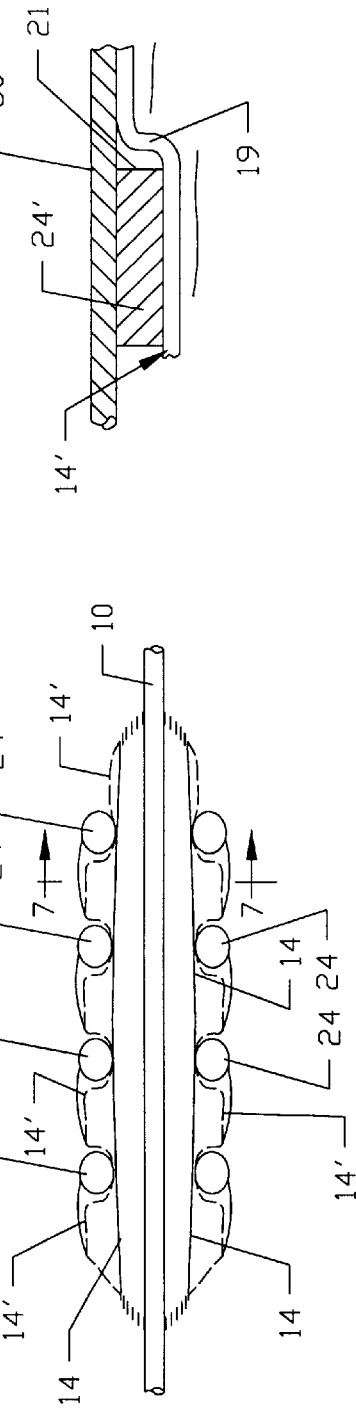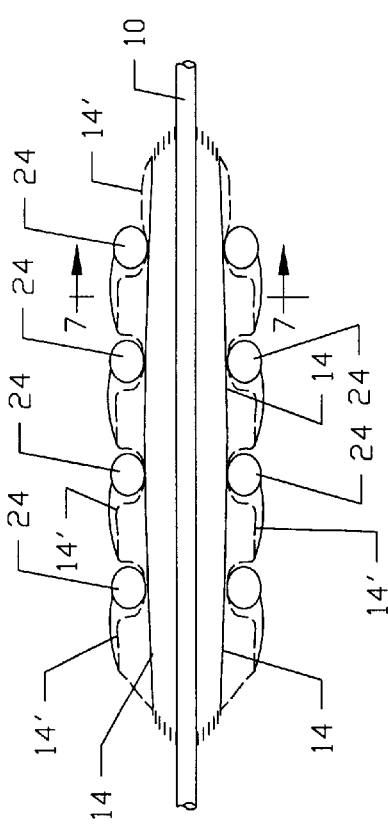

BALLOON MOUNTED STENT AND METHOD THEREFOR

FIELD OF THE INVENTION

This invention relates to stents for placement in the human body and delivery systems therefor.

BACKGROUND OF THE INVENTION

The use of intraluminal stents has had increasing acceptance and use in the treatment of various medical conditions. Intraluminal stents can be used to maintain the patency of blood vessels and other body lumens, such as in the treatment of urological disorders, among others. The use of stents to maintain open a coronary or other artery after an angioplasty procedure has been performed has become a common practice. Over the past decade, various stent designs have been described and used. Many have been of the type in which the stent is in a tubular configuration that can be expanded from a relatively small diameter adapted for delivery through the vasculature (low profile) to a larger deployed diameter by mounting the stent on the balloon of an inflatable balloon catheter and then advancing the catheter to place the balloon mounted stent at the intended site of deployment. The balloon then is inflated to expand the stent into engagement with the body lumen. The stent maintains its expanded shape to support the body lumen. The balloon then is deflated and the delivery catheter is withdrawn, leaving the stent in place to support the body lumen. The configuration of such stents typically may be considered as generally tubular in which the wall of the tube is defined by variously configured wires or a tubular member that has been shaped to provide a plurality of interconnected wire-like struts or wires. Illustrative examples of such stents may be found in U.S. Pat. No. 4,733,665 U.S. Pat. No. 5,104,404 (Wolff), U.S. Pat. No. 5,421,955 (Lau) and in International Publication WO 96/41591 (Borghi), among others.

The design and placement of a stent can present a number of considerations, particularly when the stent is to be used in an environment where it must be advanced through tortuous anatomy, as is not uncommon in coronary angioplasty. The stent must have the ability to maintain its tubular configuration when expanded in the body lumen in order to maintain the body lumen open. It also should have sufficient longitudinal flexibility, when mounted in its low profile on the balloon, so that it can be advanced through curved, sometimes tortuous, blood vessels in order to reach the deployment site. Additionally, the position of the stent on the balloon should be maintained without shifting longitudinally, as the balloon mounted stent is advanced to the deployment site. That can present particular difficulty when the stent and balloon to which it is mounted must be passed through sharply curved tortuous anatomy or anatomy where the lumen has become narrowed or otherwise partly obstructed regions. Should the stent engage a blood vessel in a sharply curved or somewhat narrowed region and consequently, shift longitudinally on the balloon as the catheter is advanced or manipulated, the balloon, when inflated, may not expand the stent fully along the length of the stent. In some cases, the stent could be dislodged from the balloon without the ability to retrieve it.

The importance of maintaining the stent securely on the balloon has been recognized in the prior art. A number of approaches have been proposed. Some simply slide the stent onto the balloon and crimp it tightly about the balloon. That may risk damage to the balloon or the stent and also may result in a relatively longitudinally stiff stent. Other stent retention devices have been proposed including the use of a sleeve to overlie the stent during advancement, with the sleeve being retracted when the stent is to be deployed. Still other approaches have included the use of end caps mounted on the catheter and adapted to temporarily engage the ends of the stent while permitting the stent ends to release when the stent is expanded as is shown in U.S. Pat No. 4,950,227 (Savin). Such devices and techniques generally have required compromises of one or more desirable features of the stent. The desirable low profile or longitudinal flexibility may be compromised as well as the security of retention. It would be desirable to provide a balloon mounted stent and method for such mounting that would reduce the extent of compromise of desirable characteristics of the stent and its delivery system.

SUMMARY OF THE INVENTION

In accordance with the invention, a stent and balloon catheter assembly is provided in which after the stent is mounted on the balloon that has been wrapped about the catheter shaft in a relatively tight, low profile, the balloon is molded against the stent to secure the stent directly to the balloon. The outer diameter of the stent is maintained during the process, as by placing a rigid retaining tube about the stent. The interior of the balloon then is pressurized sufficiently so that, although wrapped in a low profile configuration, it will tend to expand radially outwardly against the stent. Concurrently with such pressurization, polymeric material of the balloon is softened, as by heating, exposure to a solvent or other means for softening the balloon sufficiently to enable it to be molded. The balloon material may be softened by any appropriate means including heat or solvents. The soft moldable condition of the balloon is maintained sufficiently to enable portions of the balloon to expand and mold against the ends of the stent or into interstices along the length of the stent, or both. Portions of the balloon thus are expanded to a radius that is greater than the radius of the inner lumen defined by the stent. The balloon is maintained under conditions of pressure and softened condition for a predetermined time to assure the balloon will maintain its molded state. In the resulting assembly, the stent is interengaged with portions of the balloon to provide substantial resistance to shifting of the longitudinal position of the stent along the balloon. The resistance to longitudinal shifting created by the interengaged portions supplements frictional engagement between the stent and balloon serving to resist their relative axial movement. The balloon, being longer than the stent may expand beyond the ends of the stent toward the inner diameter of the retaining tube to form a shoulder that engage the ends of the stent to provide resistance to axial movement. The balloon expansion at the ends of the stent also reduces the abruptness of the transition between the balloon and the end of the stent to reduce the risk of snagging the stent on the guide catheter or vessel.

A general object of the invention is to provide an improved system for mounting a stent securely onto the balloon of a stent delivery catheter without increasing the profile of the balloon and stent combination. Also among the objects of the invention are to provide an improved balloon-stent combination in which the stent is secured on the balloon of a stent delivery catheter by interfering engagement of the stent directly with the balloon; to provide a balloon catheter and mounted stent adapted to pass through tortuous anatomy with reduced risk of the stent being displaced from its initial position on the balloon; to provide an improved technique for mounting a stent on the balloon of a stent delivery catheter; to provide a technique for effecting direct engagement between a stent and the balloon of a delivery catheter in which the stent is securely mounted on the balloon without use of supplemental retaining or restraining devices; to provide an assembly of a stent mounted securely on the balloon of a balloon catheter without significantly affecting the longitudinal flexibility of the assembly; and to provide a method for mounting a stent on the balloon of a stent delivery catheter in which some portions of the balloon project radially beyond the radius defined by the inner surface of the stent.

DESCRIPTION OF THE DRAWINGS

The foregoing and other objects and advantages of the invention will be appreciated more fully from the following further description thereof with reference to the accompanying drawings wherein:

FIG. 1 is a diagrammatic illustration of a stent delivery catheter having a stent mounted on the balloon of a delivery catheter;

FIG. 1A is cross-sectional view of the catheter shown in FIG. 1 as seen along the line 1A—1A;

FIG. 2A is a diagrammatic transverse cross-sectional illustration of the balloon region of a balloon catheter with the balloon having been evacuated to form radially extended wings;

FIG. 2B is a diagrammatic illustration similar to FIG. 2A in which the wings of the evacuated balloon have been wrapped about the catheter shaft to a low profile configuration;

FIG. 2C is a diagrammatic illustration similar to that of FIGS. 2A and 2B but in which the balloon has been inflated;

FIG. 3 is a diagrammatic illustration of a wrapped balloon and a stent mounted on a loading tube in readiness to be placed on the balloon;

FIG. 4 is an illustration of the balloon region of the stent delivery catheter with the stent having been located on the balloon and with a tubular restraining member being advanced over the assembly of the stent and balloon;

FIG. 5 is a diagrammatic, longitudinal sectional illustration of the interfacing region between the balloon and the stent as seen along the line 5—5 of FIG. 1 in which the configuration of the interfacing region before pressure molding is shown in solid lines, and the configuration of the interfacing region after pressure molding is shown in phantom;

FIG. 5A is a diagrammatic longitudinal sectional illustration of the manner in which the balloon can be molded against the ends of a stent to form shoulders engageable with the ends adapted to resist longitudinal movement of the stent on the balloon;

DESCRIPTION OF THE ILLUSTRATIVE EMBODIMENT

Figure 1B:
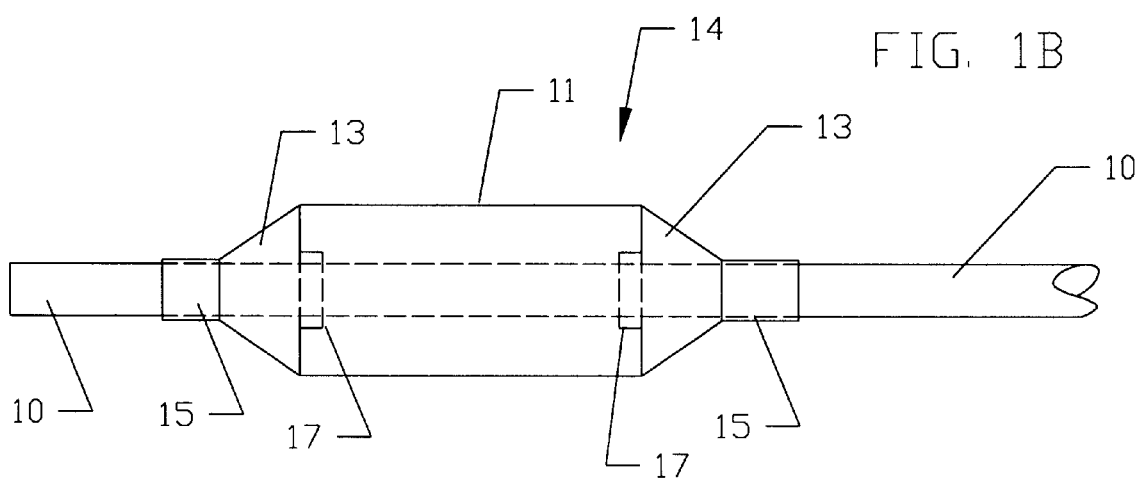
FIG. 1B is a digrammatic illustration of the distal end of the catheter showing the configuration of the balloon, when inflated, and the shaft of the catheter.

The invention, for convenience, is described in the context of a stent adapted for delivery in conjunction with an angioplasty procedure, although it should be understood that the invention may be practiced in connection with stents and catheters adapted for other medical procedures. In the preferred embodiment, the stent delivery catheter includes a catheter shaft 10 having at least one lumen 12 for inflation of a balloon 14 mounted at the distal region of the catheter shaft 10. As shown in FIG. 1B, the balloon may be configured to have a generally cylindrical, uniform diameter central section 11 and a pair of outwardly tapering end cones 13, each of which terminates in a neck 15 by which the balloon is attached to the catheter shaft 10. The portion of the catheter shaft 10 that extends through the balloon may be provided with a pair of longitudinally spaced radiopaque markers 17. The markers may be disposed on the shaft 10 at approximately the regions where the end cones 13 merge into the central balloon section 11.

The catheter shaft also may have a guidewire lumen 16 to enable the catheter to be advanced and guided to the deployment site along a guidewire 18. The proximal end of the shaft 10 is provided with a fitting 20 that includes a connector 22 by which the inflation lumen 12 can be connected to a balloon inflation device (not shown). While a dilatation catheter intended for angioplasty may be used in the practice of the present invention, it is not necessary that the balloon 14 be suitable for an angioplasty procedure as it need only be capable of retaining and expanding the stent in a delivery procedure that is separate from the angioplasty procedure. However, the balloon of the stent delivery catheter of the present invention should have characteristics that enable it to be molded into engagement with the interstices or other radially extending surfaces of the stent. For example, in the illustrative embodiment, the balloon may be that described in U.S. Pat. No. 5,500,180 (Anderson et al.).

In accordance with the invention a stent 24 having a generally tubular configuration is mounted on and about a balloon 14. The stent may be somewhat shorter than the cylindrical central section 11 of the balloon to assure that when the balloon is inflated within the patient to deploy the stent, the stent will be expanded along its length by the balloon.

Figure 6:
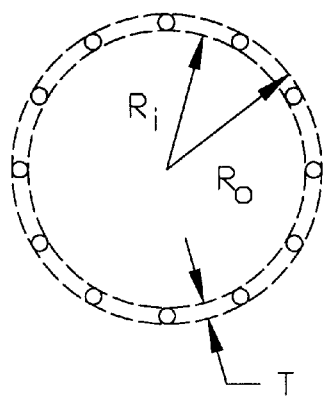
FIG. 6 is a diagrammatic transverse section through the stent illustrating the relationship of the inner radius, outer radius and virtual wall thickness defined by the stent.

The invention may be practiced with any balloon-expandable stent. For purposes of illustration, the invention is described as being used in connection with a stent described in International Patent Application, Publication WO 96/41591 (Borghi), the disclosure of which is hereby incorporated by reference, in its entirety. Other examples of balloon expandable stents include those disclosed in U.S. Pat. No. 4,733,665 (Palmaz), U.S. Pat. No. 5,041,126 (Gianturco) and U.S. Pat. No. 5,104,404 (Wolff), the disclosures of which also are hereby incorporated by reference, in their entireties. In the illustrative embodiment, the stent is characterized by an arrangement of wire-like hoops 23 connected to a spine 25 that, taken together, may be considered to define a virtual cylindrical tubular shape. The reticulated wires or struts 26 that form the stent are arranged to define spaces 27 along the length of the stent, the configuration and orientation of which may vary as a function of the geometry and design of the stent. The tubular stent thus may be considered as defining an inner cylindrical radius $R_i$ and an outer cylindrical radius $R_o$, the difference between the two radii defining what may be considered as the wall thickness T of the stent (FIG. 6). The stent may be formed by a number of techniques familiar to those skilled in the art and may be formed from a variety of materials, including metals such as stainless steel or nickel titanium alloys (e.g., nitinol), polymeric or bioabsorbable materials. The structure and material of the stent should be capable of enabling expansion from its low profile configuration, in which it is adapted to be advanced through the vasculature to the deployment site, to an expanded diameter in which it can engage and support the wall of a blood vessel or other body lumen, as appropriate.

The stent is intended to be mounted on a balloon that itself has been configured in a low profile. As shown in FIGS. 2A–2C, a common technique for configuring the balloon in a low profile is first to evacuate the balloon to cause the balloon to assume a cross-sectional shape as shown in FIG. 2A in which the balloon is collapsed and defines a plurality of radially extending flat wings 28. While maintaining the evacuation pressure, the wings of the balloon are wrapped closely about the catheter shaft in one of several compact configurations to maintain a low profile about the shaft, such as an S-shaped configuration shown in FIG. 2B.

With the balloon in its wrapped, low profile configuration, the stent then is loaded onto the wrapped balloon as suggested in FIG. 3. The stent may be positioned on the balloon so that the ends of the stent are disposed adjacent and between the radiopaque marker bands on that portion of the catheter shaft that passes through the balloon. To facilitate loading, the stent may be mounted about and crimped onto a thin wall polymeric tube, shown in phantom at 29 that, in turn, can be slipped over the balloon. The tube 29 is advanced to position the stent in the desired location relative to the balloon with the end cones 13 protruding beyond the ends of the stent. Then, while holding the stent in the desired position relative to the balloon, the tube 29 is withdrawn, leaving the stent in the desired longitudinal position about the balloon. The stent may be crimped slightly by hand or with a crimping tool to achieve a snug fit about the balloon.

A relatively rigid tube 30 then is placed over the stent. The tube 30 may be formed from a suitably rigid tubing such as a polymer commercially available under the trade designation KYNAR and is intended to restrain the stent from radial expansion during the remainder of the stent mounting process. The tube 30 should be of sufficient length to completely cover the stent and the balloon and may be of the order of twice as long as the stent. The tube 30 should be dimensioned such that a relatively small clearance exists between the inside diameter of the tube and the outside surface of the stent as, for example, on the order of 0.001"–0.003" to facilitate placement of the tube 30 over the stent. The balloon then is pressurized by connection of a suitable device to the balloon inflation leg of the proximal fitting. In the illustrative example, the balloon may be pressurized with a gas, such as air or nitrogen, within the range of 6 to about 20 bar, preferably about 10 bar. Although the balloon has been wrapped tightly in a low profile configuration, the wrapping cannot completely seal off all minute flow passages through the balloon. Consequently, it is possible to apply sufficient pressure within the wrapped balloon to cause portions of the balloon to press radially outwardly against the stent.

Figure 7:
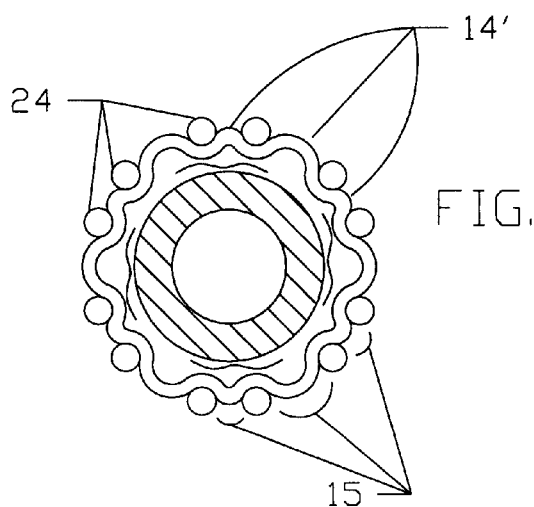
FIG. 7 is a transverse sectional illustration of the balloon mounted stent as seen along the line 7—7 of FIG. 5 showing the manner in which portions of the balloon protrude radially beyond the inner radius of the stent and into engagement with radially extending surfaces of the stent.

In the illustrative embodiment, the assembly of the pressurized balloon catheter, stent and molding tube 30 then is heated to raise the temperature of the balloon material sufficiently to allow it to yield and be molded around the ends and against the interior of the stent. A temperature in the range of 50°–70° C., preferably 65° C., under the above pressures has been found to be sufficient to cause the balloon to become molded to the stent. Although the expansion of the balloon may be slight, it is sufficient to cause some portions of the balloon to expand to a radius that is greater than the inner radius $R_i$ of the stent so that those portions of the balloon may be considered as projecting radially outwardly into the region of the virtual wall thickness T. The conditions of temperature and pressure are maintained sufficiently long to assure that the balloon will set and remain in that configuration when the balloon is cooled and pressure is removed. FIG. 7 is a transverse sectional illustration of the balloon mounted stent after the balloon has been molded and expanded radially outwardly so that portions of the balloon, indicated at 14' protrude radially outwardly beyond the inner radius $R_i$, of the stent as defined by the struts 26. FIG. 5 is a longitudinal illustration of the balloon and stent of FIG. 7. FIG. 5A illustrates, diagrammatically and in enlarged scale, the region of the molded balloon with the end of a stent as confined within the retaining tube. The shoulder thus formed enables the balloon to engage directly the ends of the stent to resist longitudinal movement of the stent on the balloon. This embodiment may be used with any type of stent, including stents that have few or no interstices when in the low profile configuration.

Applicants have found that, in the illustrative embodiment, applying heat and temperature for a time of approximately 30–90 seconds, preferably about 60 seconds, sufficiently molds the balloon to the stent. A brief cooling period of approximately one minute immediately following the heating period, while maintaining pressure at 10 bar also may help set the balloon in its molded configuration. Although the balloon and stent may expand slightly to contact the inside of the tube 30 while pressure is applied, slight elastic recoil of the stent after the inflation pressure is removed results in a slight clearance on the order of 0.0005" between the tube and the stent. The restraining tube 30 then is easily removed and the stent and balloon may be recompressed about the catheter shaft by hand, or with a suitable tool to reduce the slight expansion that occurred during the balloon/stent engagement process. The delivery catheter with premounted stent then may be packaged in readiness for use in a procedure.

It should be understood that although, in the illustrative embodiment, the balloon material is softened by the application of heat, other procedures may be employed to soften the balloon in the practice of the invention. For example, the balloon material may be softened, where appropriate, with a solvent sufficiently and under conditions to enable the balloon to be molded under the influence of the pressure differential from the interior to the exterior of the balloon.

From the foregoing, it will be appreciated that the invention provides a balloon mounted stent and a method for mounting the stent on the balloon in which there are no stent retaining components to increase the profile of the assembly while maintaining the stent in a secure position on the balloon by direct, interfering engagement of the stent with the balloon. The invention provides a balloon catheter and mounted stent in which the longitudinal flexibility is not adversely affected and that can pass through tortuous or restricted anatomy with reduced risk of the stent becoming dislodged or displaced from its position on the balloon. A number of advantages thus are achieved with minimal compromise. It should be understood, however, that the foregoing description of the invention is intended merely to be illustrative thereof and that other embodiments, modifications and equivalents within the scope of the invention may be made by those skilled in the art.

Having thus described the invention, what we desire to claim and secure by Letters Patent is:

1. A method for mounting a stent on a balloon of a catheter comprising:

configuring the balloon in a low profile;

placing a balloon expandable stent on the balloon;

expanding portions of the balloon radially outward to a radius greater than the inner radius of the stent to resist longitudinal movement of the stent relative to the balloon while in said low profile;

wherein the step of expanding portions of the balloon radially outwardly comprises molding at least part of the balloon radially outwardly into engagement with and against the inner contour of the stent by concurrently applying pressure to the interior of the balloon and softening the balloon material sufficiently to enable it to be molded against the inner contour of the stent under the influence of said pressure, wherein the softening of the balloon material is accomplished by applying a solvent to the balloon material; and maintaining the softened balloon in the pressurized condition, sufficiently to cause portions of the balloon to be molded radially outwardly against and in conformity to at least a portion of the inner contour of the stent.

2. A method as defined in claim 1 further comprising:

while maintaining the pressure in the balloon, allowing the balloon to set to a molded configuration that includes a shoulder adjacent and engageable with at least one end of the balloon.

3. A method as defined in claim 1 further comprising maintaining the diameter of the stent while the balloon is pressurized.

4. A method as defined in claim 3 wherein the step of maintaining the stent diameter comprises placing a restraining member about the exterior of the stent before the interior of the balloon is pressurized.

5. A method as defined in claim 4 wherein the step of maintaining the diameter of the stent comprises placing a rigid tubular member over the stent.

\* \* \* \* \*

UNITED STATES PATENT AND TRADEMARK OFFICE
CERTIFICATE OF CORRECTION

PATENT NO. : 5,976,181
DATED : Nov. 2, 1999
INVENTOR(S) : Whelan et al.

It is certified that error appears in the above-identified patent and that said Letters Patent is hereby corrected as shown below:

On the Title page, in item [75], the residence of Neil Purcell, "Gallway", should read --Galway--.

Signed and Sealed this

Eighth Day of August, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 5,976,181
DATED : November 2, 1999
INVENTOR(S) : Whelan et al.

Page 1 of 1

It is certified that error appears in the above-identified patent and that said Letters Patent is hereby corrected as shown below:

<u>Title page,</u>
Item [73], "Santa Rosa, Calif." should read -- Dublin, Ireland. --

Signed and Sealed this

Thirtieth Day of December, 2003

JAMES E. ROGAN
*Director of the United States Patent and Trademark Office*